United States Patent [19]

El-Zaatari et al.

[11] Patent Number: 5,776,692

[45] Date of Patent: Jul. 7, 1998

[54] MYCOBACTERIAL GENUS-SPECIFIC DNA PROBE AND ITS EXPRESSED PRODUCT

[75] Inventors: Fouad A. K. El-Zaatari, Pearland, Tex.; Saleh Naser, Orlando, Fla.; David Y. Graham, Houston, Tex.

[73] Assignee: Baylor College of Medicine, Houston, Tex.

[21] Appl. No.: 447,965

[22] Filed: May 23, 1995

[51] Int. Cl.$^6$ .............................. C12Q 1/68; C12P 19/34; C07H 21/04; C12N 15/00

[52] U.S. Cl. .................. 435/6; 435/91.2; 435/320.1; 536/22.1

[58] Field of Search ............... 435/320.1, 6, 91.2; 536/22.1

[56] References Cited

U.S. PATENT DOCUMENTS

| | | | |
|---|---|---|---|
| 4,918,178 | 4/1990 | Hurley et al. | 536/27 |
| 4,965,192 | 10/1990 | Maes | 435/7 |
| 5,225,324 | 7/1993 | McFadden et al. | 435/6 |
| 5,314,801 | 5/1994 | Nycz et al. | 435/6 |
| 5,352,580 | 10/1994 | Spears et al. | 435/6 |
| 5,354,691 | 10/1994 | Van Eden et al. | 436/506 |
| 5,370,998 | 12/1994 | Crawford et al. | |

FOREIGN PATENT DOCUMENTS 0 619 375 A2 10/1994 European Pat. Off. .......... C12Q 1/68

OTHER PUBLICATIONS

P.D. Butcher, J.J. McFadden, and J. Hermon-Taylor; Investigation of mycobacteria in Crohn's disease tissue by southern blotting and DNA hybridisation with cloned mycobaterial genomic DNA probes from a Crohn's disease isolated mycobacteria; Gut 29: 1222–1228 (1988).

Böddinghaus, Rogall, Flohr, Blöcker, and Böttger; Detection and Identification of Mycobacteria by Amplification of rRNA; Journal of Clinical Microbiology; Aug. 1990, pp. 1751–1759.

Takewaki, Okuzumi, Ishiko, Nakahara, Ohkubo, and Nagai; Genus–Specific Polymerase Chain Reaction for the Mycobacterial dnaJ Gene and Species–Specific Oligonucleotide Probes; Journal of Clinical Microbiology, Feb., 1993, pp. 446–450.

Poupart, Coene, Van Heuverswyn, Cocito; Preparation of a Specific RNA Probe for Detection of Mycobacterium paratuberculosis and Diagnosis of Johne's Disease; Journal of Clinical Microbiology, Jun., 1993, vol 31(6), pp. 1601–1605.

El-Zaatari et al. Identification of *Mycobacterium avium* Complex in Sarcoidosis, vol. 34(9), pp. 2240–2245, 1996.

*Primary Examiner*—Kenneth R. Horlick
*Assistant Examiner*—Joyce Tung
*Attorney, Agent, or Firm*—Fulbright & Jaworski LLP

[57] ABSTRACT

Recombinant clone pMptb #48 expressing a 36k *M. paratuberculosis* antigen is provided that provides a more sensitive and discriminating test than those in which crude antigens have been used. A mycobacterial genus-specific DNA probe corresponding to a 1.4 kb BamH1-DNA insert in pMptb #48 is also provided. The 1.4 kb insert includes the entire DNA coding sequence for an *M. paratuberculosis* 36k protein. There is also provided methods for serologically testing specimens which include the use of recombinant clone pMptb #48 and/or the p36k protein and/or fragments of the p36k protein. Also provided are methods for identifying mycobacterial infections using a probe corresponding to the 1.4 kb DNA sequence shown in FIG. 4, the coding portion of the 1.4 kb DNA sequence, or fragments thereof.

5 Claims, 7 Drawing Sheets

| Disease | No. of positives / No. tested (%) |
|---|---|
| Tuberculosis | 4/06 (67) |
| Leprosy | 6/06 (100) |
| Crohn's disease | 22/27 (81) |
| Sarcoidosis | 5/05 (100) |
| Normal (BCG positive) | 4/04 (100) |
| Normal (BCG negative) | 0/02 (0) |
| Ulcerative colitis | 9/17 (53) |
| Non-inflammatory bowel disease[a] | 4/15 (27) |

[a] patients with gastric or duodenal ulcer disease.

FIG. 3

| | Bacterial Strains | Results of Hybridization |
|---|---|---|
| 1. | *M. para* ATCC 19698 | + |
| 2. | *M. para* (Linda) ATCC 43015 | + |
| 3. | *M. para* (BEN) ATCC 43544 | + |
| 4. | *M. para* C286 | + |
| 5. | *MAC*, serotype 18 | + |
| 6. | *MAC*, serotype 7 | + |
| 7. | *MAC*, serotype 2 | + |
| 8. | *MAC*, serotype 9 | + |
| 9. | *MAC*, serotype 21 | + |
| 10. | *MAC*, serotype 19 | + |
| 11. | *MAC*, WP VI-72 | + |
| 12. | *M. tuberculosis*, VA strain | + |
| 13. | *M. Tuberculosis* ATCC 2177 | + |
| 14. | *M. chelonae* | + |
| 15. | *M. kansasii* | + |
| 16. | *M. phlei* | + |
| 17. | *M. fortuitum* | + |
| 18. | *M. smegmatis* ATCC 27199 | + |
| 19. | *M. smegmatis* ATCC 607 | + |
| 20. | *Nocardia asteroides* | -ve |
| 21. | *E. coli*, vector | -ve |
| 22. | *S. epidermidis* | -ve |
| 23. | *S. aureus* | -ve |
| 24. | *P. aeruginosa* | -ve |
| 25. | *C. jejuni* | -ve |
| 26. | *C. diversus* | -ve |
| 27. | *H. pylori* | -ve |
| 28. | *S. viridans* | -ve |
| 29. | *M. moranii* | -ve |
| 30. | *K. pneum* ATCC 13883 | -ve |
| 31. | *S. flexneri* | -ve |
| 32. | *S. Marcescens* | -ve |
| 33. | *P. mirabilis* | -ve |
| 34. | *E. faecalis* | -ve |
| 35. | *V. parahaemolyticus* | -ve |
| 36. | *V. cholerae* | -ve |
| 37. | *A. calcoaceticus* | -ve |
| 38. | *A. xylosoxidas* | -ve |

FIG. 4

```
   1 gaTCCCGACA CCACGTGGCC GTCCGCGGAG GTCACCCGGT AGTTGGCCGT
  51 GTAGGTCCCG GCCGGCCCCA GCGGGCGCAC CGCCACGCTG ACCACCGCGT
 101 CCTGCACGGT GGGCTCTCCG GTGGACCACA CGTTGCCGTC CGGCCCGACC
 151 ACCGTaATCG CGGCGAAGGT GGTTTGCAGC TGTTCGTTGA AGGTCGcGCT
 201 GACCCGGTGC GGCCCGGTCG TnAGCGCCGC tTCGGCGGCG GTnTCGGTCG
 251 CCACCCGGnC GGCGTGCGCC CACGACGCGG GCGCGGTCAG CCCGGCGATC
 301 AGGACCAGGG CGCCGACGCA CGCGCCAACC GCCCAGCGCC TCATGCCCGC
 351 CGGCGGACCA GGGCGATCGC GATGCCCAGC GCGGCCAGCA CCAGCGCGGC
 401 GCCGCCCAGC CACCGCgCGG CGTTGTCGGC CGCGGCGGGT CCGCCGGGGT
 451 GCTGGTGGCC GGcCGCCGGC CGGCGGCAGG GCGAGCgTCG GGGCCGGGTG
 501 CTCGGGCTCG CCGCCGTCGG GCAGCGGtGG CTGATCCCAC TTgACCACGG
 551 TGCCGTCGGC GTAGGTcTGG nTGGCCGGAA AgCTGACGGT GTCGGCGTCG
 601 GGCAGCTTCA CCGACAGCCG GAACAGGGCG AACTGGTCGG GCCCGATGCC
 651 GCCGCCCGCG GGGGTtCCCA GGTGACCGAG CGGACGGTGC CGGATGCCGC
 701 GTcCCGGTCC AGCCGGGCCG TCCAGCCCGG CATGGTCTCG GTGTGCGCCG
 751 CGGCCACGTT GGGCAGCGCG ACGGTCAGCG CGGTGGTGGC GGCCCCGGTG
 801 TTCGATTCGT TGGGCACCTG GAAGGTGACG ACGGCCATGg CGCCGCGCAC
 851 CGGGTTGTCG CTGCCGGCGT GCACGTGCGC CGACGCCATC GGGGACCAGG
 901 CCACCGATCC CAGGCACAGG GCGGCGACGG CgACCAGCAG GCGCGGGGCC
 951 CGGCGCTTGC gCGGCGGCAT GCGGGTAGCT CAACCcGAGG CGGGCCATCA
1001 GGTCCGCcTc GATGCCGTCg AGCTgCgAGG AGATGGCGGC GTGTCCCGCC
1051 cGGcGCCGGG CGGCGGGCAT GTTCTCCGCG GCGGTCACCG CGGCCGCcAG
1101 GTCGGTgAGC CGCTCGGAGA TGGCGGCgAC GAACTGCTTG GTCTCGCCGT
1151 CCTTGGTTTG CgTTCCTGCA CCAgcCGCAA CGACTTCTCC GcCCCGGCgA
1201 TGCGGGCCGA CAGCTGGGCG CCGTGGCCGG AGAACTGGCC GATCTGGGCC
1251 AACGGgACGC CCAGCCGATC GGCGCGGCGC TGGTCGATCA gCGcGcgCgC
1301 CGAGACGGGG CGCGGTAGAc GaAcGGGgTg AGGATCGGGG CGAACAgccg
1351 gacaacgtga ggtccgagct cggtacaagt tggatgatag ttgatttctt
1401 tg
```

FIG. 5A

```
        gaTCCCGACACCACGTGGCCGTCCGCGGAGGTCACCCGGTAGTTGGCCGTGTAGGTCCCG
  1     ---------+---------+---------+---------+---------+---------+  60
        ctAGGGCTGTGGTGCACCGGCAGGCGCCTCCAGTGGGCCATCAACCGGCACATCCAGGGC

S   R   H   H   V   A   V   R   G   G   H   P   V   V   G   R   V   G   P  -

GCCGGCCCCAGCGGGCGCACCGCCACGCTGACCACCGCGTCCTGCACGGTGGGCTCTCCG
  61    ---------+---------+---------+---------+---------+---------+ 120
        CGGCCGGGGTCGCCCGCGTGGCGGTGCGACTGGTGGCGCAGGACGTGCCACCCGAGAGGC

R   P   Q   R   A   H   R   H   A   D   H   R   V   L   H   G   L   S  -

GTGGACCACACGTTGCCGTCCGGCCCGACCACCGTaATCGCGGCGAAGGTGGTTTGCAGC
 121    ---------+---------+---------+---------+---------+---------+ 180
        CACCTGGTGTGCAACGGCAGGCCGGGCTGGTGGCAtTAGCGCCGCTTCCACCAAACGTCG

G   P   H   V   A   V   R   P   D   H   R   N   R   G   E   G   G   L   Q  -

TGTTCGTTGAAGGTCGcGCTGACCCGGTGCGGCCCGGTCGTnAGCGCCGCtTCGGCGGCG
 181    ---------+---------+---------+---------+---------+---------+ 240
        ACAAGCAACTTCCAGCgCGACTGGGCCACGCCGGGCCAGCAnTCGCGGCGaAGCCGCCGC

F   V   E   G   R   A   D   P   V   R   P   G   R   ?   R   R   F   G   G  -

GTnTCGGTCGCCACCCGGnCGGCGTGCGCCCACGAAGCGGGCGCGGTCAGCCCGGCGATC
 241    ---------+---------+---------+---------+---------+---------+ 300
        CAnAGCCAGCGGTGGGCCmGCCGCACGCGGGTGCTGCGCCCCGCGCCAGTCGGGCCGCTAG

?   G   R   H   P   ?   G   V   R   P   R   R   G   R   G   Q   P   G   D   Q  -

AGGACCAGGGCGCCGACGCACGCGCCAACCGCCCAGCGCCTCATGCCCGCCGGCGGACCA
 301    ---------+---------+---------+---------+---------+---------+ 360
        TCCTGGTCCCGCGGCTGCGTGCGCGGTTGGCGGGTCGCGGAGTACGGGCGGCCGCCTGGT

D   Q   G   A   D   A   R   A   N   R   P   A   P   H   A   R   R   R   T   R  -

GGGCGATCGCGATGCCCAGCGCGGCCAGCACCAGCGCGGCGCCGCCCAGCCACCGCgCGG
 361    ---------+---------+---------+---------+---------+---------+ 420
        CCCGCTAGCGCTACGGGTCGCGCCGGTCGTGGTCGCGCCGCGGCGGGTCGGTGGCGcGCC

A   I   A   M   P   S   A   A   S   T   S   A   A   P   P   S   H   R   A   A  -

CGTTGTCGGCCGCGGCGGGTCCGCCGGGGTGCTGGTGGCCGGcCGCCGGCCGGCGGCAGG
 421    ---------+---------+---------+---------+---------+---------+ 480
        GCAACAGCCGGCGCCGCCCAGGCGGCCCCACGACCACCGGCCgCGGCCGGCCGCCGTCC

L   S   A   A   A   G   P   P   G   C   W   W   P   A   A   G   R   R   Q   G  -

GCGAGCgTCGGGGCCGGGTGCTCGGGCTCGCCGCCGTCGGGCAGCGGtGGCTGATCCCAC
 481    ---------+---------+---------+---------+---------+---------+ 540
        CGCTCGcAGCCCCGGCCCACGAGCCCGAGCGGCGGCAGCCCGTCGCCaCCGACTAGGGTG

```
     TTgACCACGGTGCCGTCGGCGTAGGTcTGGnTGGCCGGAAAgCTGACGGTGTCGGCGTCG
541  ---------+---------+---------+---------+---------+---------+600
     AAcTGGTGCCACGGCAGCCGCATCCAgACCnACCGGCCTTTcGACTGCCACAGCCGCAGC

D   H   G   A   V   G   V   G   L   ?   G   R   K   A   D   G   V   G   V   G -
                                                          A
                                                          p
                                                          a
                                                          I
     GGCAGCTTCACCGACAGCCGGAACAGGGCGAACTGGTCGGGCCCGATGCCGCCGCCCGCG
601  ---------+---------+---------+---------+---------+---------+660
     CCGTCGAAGTGGCTGTCGGCCTTGTCCCGCTTGACCAGCCCGGGCTACGGCGGCGGGCGC

Q   L   H   R   Q   P   E   Q   G   E   L   V   G .  P   D   A   A   A   R   G -

GGGGTtcCCAGGTGACCGAGCGGACGGTGCCGGATGCCGCGTcCCGGTCCAGCCGGGCCG
661  ---------+---------+---------+---------+---------+---------+720
     CCCCAagGGTCCACTGGCTCGCCTGCCACGGCCTACGCACAgGGCCAGGTCGGCCCGGC

G   S   Q   V   T   E   R   T   V   P   D   A   A   S   R   S   S   R   A   V -

TCCAGCCCGGCATGGTCTCGGTGTGCGCCGCGGCCACGTTGGGCAGCGCGACGGTCAGCG
721  ---------+---------+---------+---------+---------+---------+780
     AGGTCGGGCCGTACCAGAGCCACACGCGGCGCCGGTGCAACCCGTCGCGCTGCCAGTCGC

Q   P   G   M   V   S   V   C   A   A   A   T   L   G   S   A   T   V   S   A -

CGGTGGTGGCGGCCCCGGTGTTCGATTCGTTGGGCACCTGGAAGGTGACGACGGCCATGg
781  ---------+---------+---------+---------+---------+---------+840
     GCCACCACCGCCGGGGCCACAAGCTAAGCAACCCGTGGACCTTCCACTGCTGCCGGTACc

V   V   A   A   P   V   F   D   S   L   G   T   W   K   V   T   T   A   M   A -

CGCCGCGCACCGGGTTGTCGCTGCCGGCGTGCACGTGCGCCGACGCCATCGGGGACCAGG
841  ---------+---------+---------+---------+---------+---------+900
     GCGGCGCGTGGCCCAACAGCGACGGCCGCACGTGCACGCGGCTGCGGTAGCCCCTGGTCC

P   R   T   G   L   S   L   P   A   C   T   C   A   D   A   I   G   D   Q   A -
                                                                              A
                                                                              p
                                                                              a
                                                                              I
     CCACCGATCCCAGGCACAGGGCGGCGACGGCgACCAGCAGGCGCGGGGCCCGGCGCTTGC
901  ---------+---------+---------+---------+---------+---------+960
     GGTGGCTAGGGTCCGTGTCCCGCCGCTGCCGcTGGTCGTCCGCGCCCCGGGCCGCGAACG

```
            S
            p
            h
            I
      gCGGCGGCATGCGGGTAGCTCAACCcGAGGCGGGCCATCAGGTCCGCCTcGATGCCGTCg
961   ---------+---------+---------+---------+---------+---------+ 1020
      cGCCGCCGTACGCCCATCGAGTTGGgCTCCGCCCGGTAGTCCAGGCGgAgCTACGGCAGc

G  G  M  R  V  A  Q  P  E  A  G  H  Q  V  R  L  D  A  V  E -

AGCTgCgAGGAGATGGCGGCGTGTCCCGCCcGGcGCCGGGCGGCGGGCATGTTCTCCGCG
1021  ---------+---------+---------+---------+---------+---------+ 1080
      TCGAcGcTCCTCTACCGCCGCACAGGGCGGgCCgCGGCCCGCCGCCCGTACAAGAGGCGC

L  R  G  D  G  G  V  S  R  P  A  P  G  G  G  H  V  L  R  G -

N
            o
            t
            I
      GCGGTCACCGCGGCCGCcAGGTCGGTgAGCCGCTCGGAGATGGCGGCgACGAACTGCTTG
1081  ---------+---------+---------+---------+---------+---------+ 1140
      CGCCAGTGGCGCCCGCGgTCCAGCCAcTCGGCGAGCCTCTACCGCCGcTGCTTGACGAAC

G  H  R  G  R  Q  V  G  E  P  L  G  D  G  G  D  E  L  L  G -

GTCTCGCCGTCCTTGGTTTGCgTTCCTGCACCAgcCGCAACGACTTCTCCGcCCCGGCgA
1141  ---------+---------+---------+---------+---------+---------+ 1200
      CAGAGCGGCAGGAACCAAACGcAAGGACGTGGTcGGCGTTGCTGAAGAGGCgGGGCCGcT

L  A  V  L  G  L  R  S  C  T  S  R  N  D  F  S  A  P  A  M -

TGCGGGCCGACAGCTGGGCGCCGTGGCCGGAGAACTGGCCGATCTGGGCCAACGGgACGC
1201  ---------+---------+---------+---------+---------+---------+ 1260
      ACGCCCGGCTGTCGACCCGCGGCACCGGCCTCTTGACCGGCTAGACCCGGTTGCCcTGCG

R  A  D  S  W  A  P  W  P  E  N  W  P  I  W  A  N  G  T  P -

CCAGCCGATCGGCGCGGCGCTGGTCGATCAgCGcGcGcGCCGAGACGGGGCGCGGTAGAc
1261  ---------+---------+---------+---------+---------+---------+ 1320
      GCTCGGCTAGCCGCGCCGCGACCAGCTAGTcGCgCgCgCGGCTCTGCCCCGCGCCATCTg

S  R  S  A  R  R  W  S  Q  S  A  R  A  E  T  G  R  G  R  R -

GaAcGGGgTgAGGATCGGGGCGAAcAgccggacaacgtgaggtccgagctcggtacaagt
1321  ---------+---------+---------+---------+---------+---------+ 1380
      CtTgCCCcAcTCCTAGCCCCGCTTgTcggcctgttgcactccaggctcgagccatgttca

T  G  *  G  S  G  R  T  A  G  Q  R  E  V  R  A  R  Y  K  L - tggatgatagttgatttctttg
1381  ---------+---------+-- 1402
      acctactatcaactaaagaaac
```

MYCOBACTERIAL GENUS-SPECIFIC DNA PROBE AND ITS EXPRESSED PRODUCT

BACKGROUND OF THE INVENTION

1. Field of the Invention

This invention relates to recombinant clones specific to the genus Mycobacterium and their expression products. This invention also relates to methods for diagnosing mycobacterial infections using Mycobacterium-specific recombinant clones and their expression products.

2. Related Technology

The genus Mycobacterium consists of a diverse group of acid-fast bacilli including a number of important human and animal pathogens. Until recently, the three human pathogens *M. tuberculosis, M. leprae,* and *M. bovis* have been the most studied mycobacterial species. However, in immunocompromised patients, a number of opportunistic pathogens from the genus Mycobacterium have emerged, most notably disseminated *M. avium* infection in AIDS patients. In addition, there has also been a marked resurgence of human tuberculosis related to the AIDS epidemic.

The definitive diagnosis of mycobacterial infections require the isolation by culture. Pathogenic mycobacteria grow very slowly (up to six weeks in culture) and some even require animals or tissues to support their growth. Furthermore, standard protocols for definite identification include complex and time consuming procedures, especially for nontuberculous mycobacteria, which can further delay identification by several weeks.

With the emergence of an increasingly large proportion of multiple drug resistant strains of *M. tuberculosis,* rapid isolation and identification methods are essential for proper and efficient delivery of medical care. In a clinical laboratory setting, it would be very helpful if suspected mycobacteria-containing specimens could be evaluated rapidly and accurately. Elimination of those specimens that were negative from further laboratory analysis would reduce the labor required to process these specimens and, most importantly, free these patients from unnecessary antimycobacterial therapy until the results of their culture had been obtained.

Pathogenic mycobacteria contain a complex mixture of antigens with varied antigenic determinants and there is much cross-reactivity among mycobacteria antigens and antigens from other organisms. Many of these determinants are also expressed by heterologous mycobacterial species and as a result, antibodies to one mycobacteria species often react with others, limiting the value of diagnostic tests based on detection of crude and/or native antigens. Thus, serological diagnosis of most mycobacterial infections may only be demonstrable at the epitope level.

BRIEF DESCRIPTION OF THE INVENTION

It is an object of this invention to provide recombinant clones expressing *M. paratuberculosis* antigens that provide a more sensitive and discriminating test than those in which crude antigens have been used. It is another object of the present invention to provide a mycobacterial genus-specific DNA probe. Accordingly, there is provided according to the invention recombinant clone pMptb #48. Recombinant clone pMptb #48 contains a 1.4 kb BamH1-DNA insert which includes the entire DNA coding sequence for an *M. paratuberculosis* 36k protein. Accordingly, the present invention is also considered to include the 1.4 kb BamH1-DNA insert and the 36k protein for which it codes. The present invention is also considered to include fragments of both the 1.4 kb BamH1-DNA insert and the 36k protein. For the purposes of the present invention, and with respect to the DNA sequence, the term "fragments" shall mean oligonucleotides of at least 15 nucleotides in length which code for biologically active sites on the protein or which can be used as PCR primers. With respect to the 36k protein, the term "fragments" for the purposes of the present invention shall mean peptides of at least 8 amino acids in length which contain antigenic epitopes reactive with antibodies to the whole protein.

The present invention is also considered to include methods for serologically testing specimens which include the use of recombinant clone pMptb #48 and/or the p36k protein and/or fragments of the p36k protein. The present invention is also considered to include methods for identifying mycobacterial infections using a probe corresponding to the 1.4 kb DNA sequence shown in FIG. 4, the coding portion of the 1.4 kb DNA sequence, or fragments thereof.

DESCRIPTION OF THE DRAWINGS

FIG. 4 shows the DNA sequence of the sense strand of the 1.4 kb BamH1-DNA insert.

DETAILED DESCRIPTION OF THE INVENTION

Figure 1:
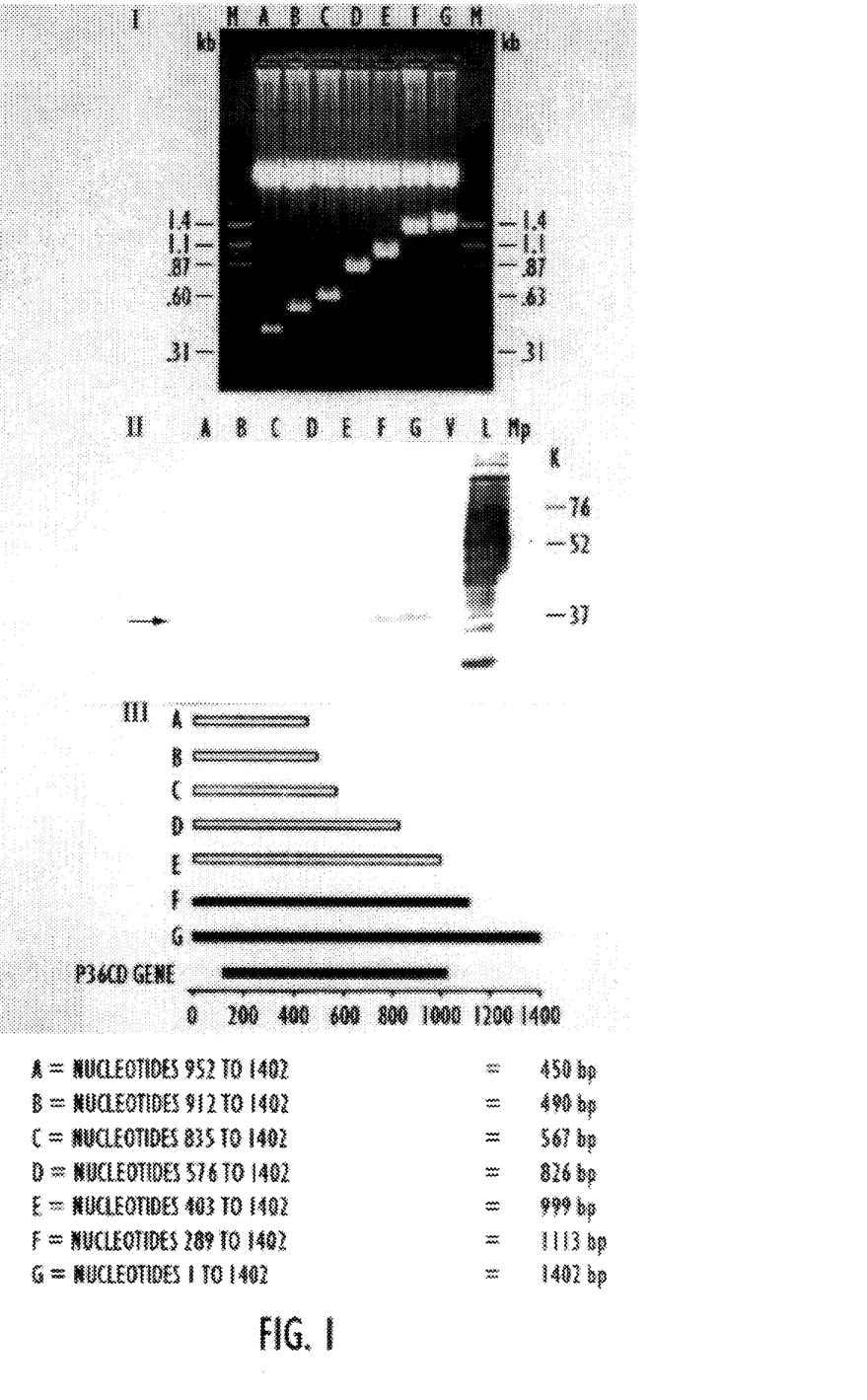
FIG. 1 is a representation of the sequencing strategy of the 1402 base pair *M. paratuberculosis* fragment containing p36 encoding-gene by nested deletion technique.
Figure 2:
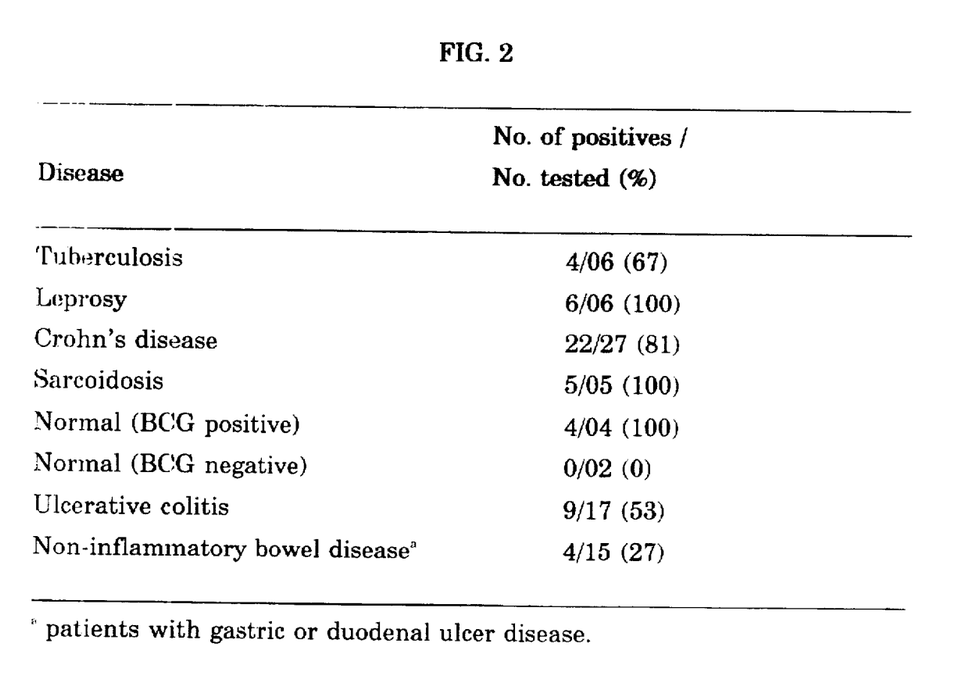
FIG. 2 is a summary of humoral immune response against *Mycobacterium paratuberculosis* p-36k recombinant clone on SDS-immunoblots.
Figure 3:
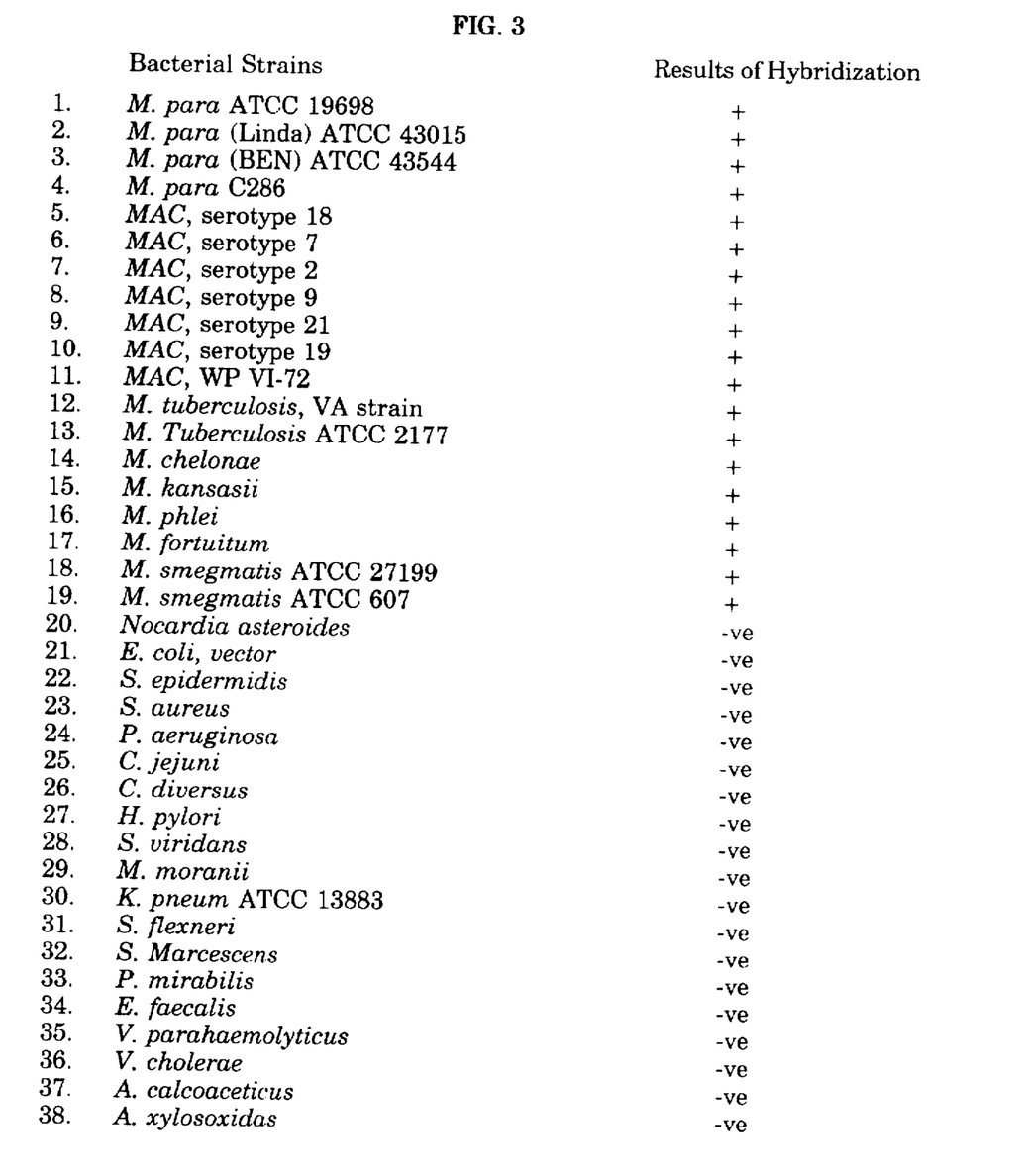
FIG. 3 shows the bacterial strains analyzed to establish the specificity of the mycobacterial genus-probe.
Figure 5B:
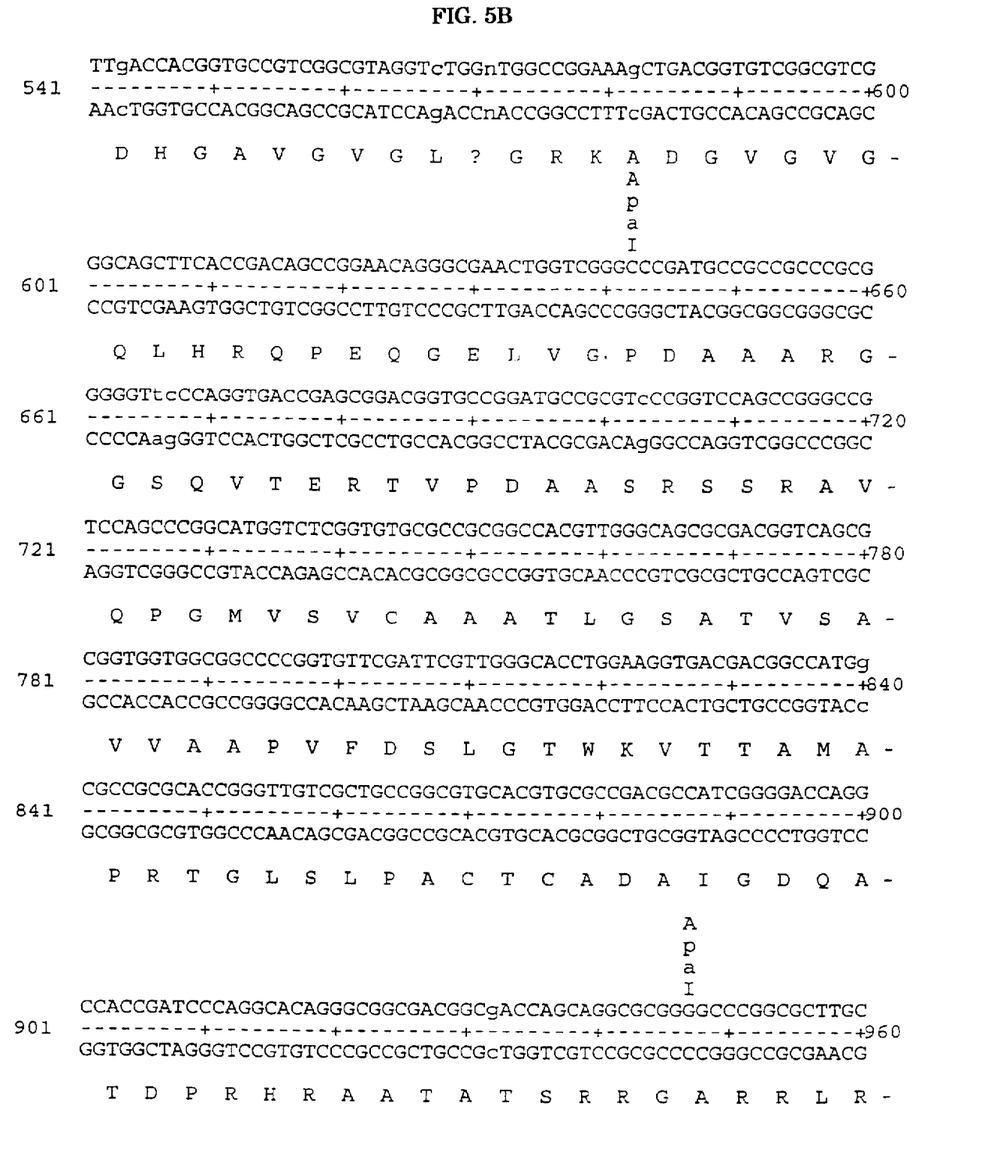
FIG. 5 is a linear map of the region that contains the p36K encoding gene together with the putative amino acid sequence for which it codes.
Figure 5C:
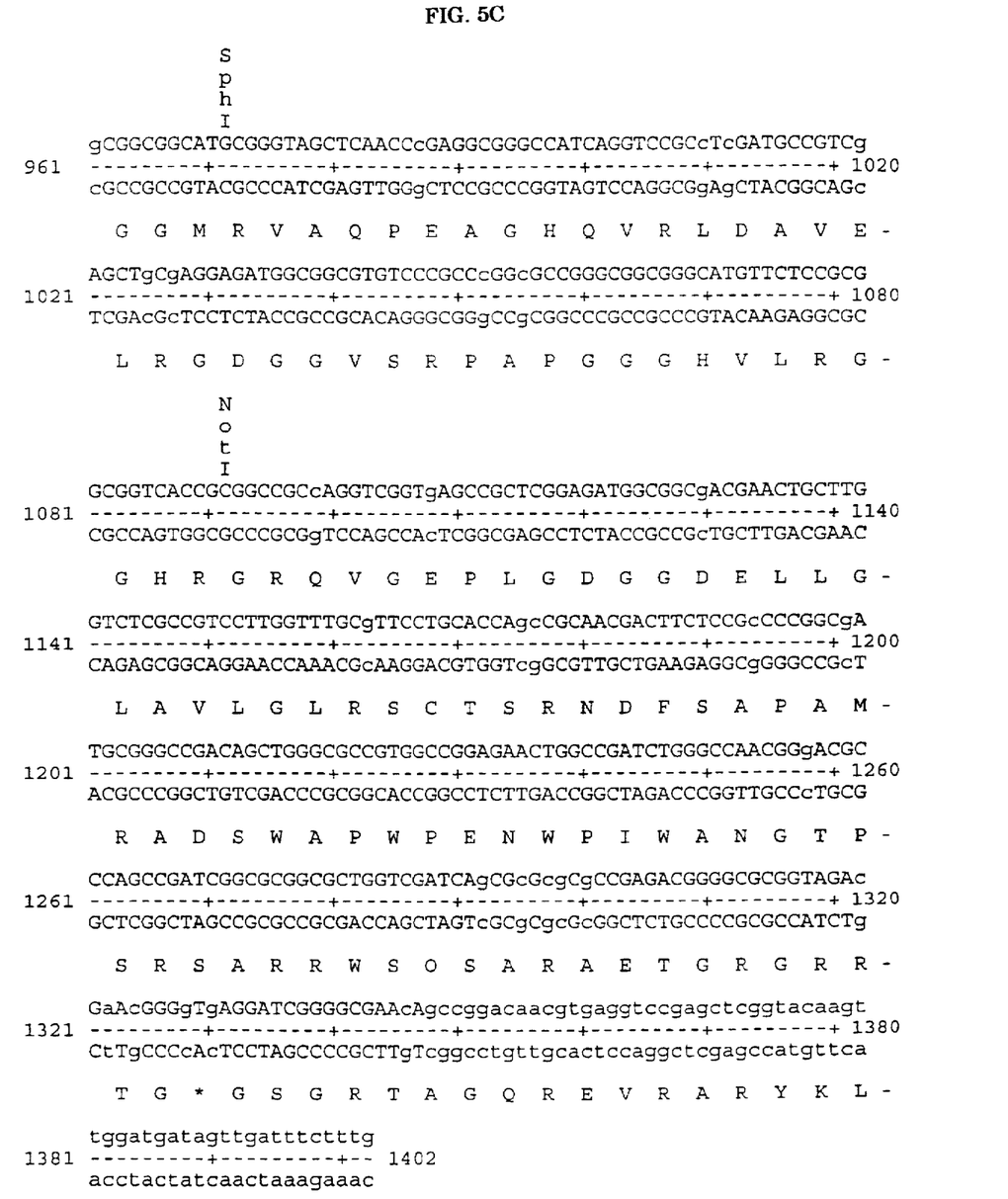

We isolated, sequenced and characterized a recombinant clone pMptb #48, expressing a 36K antigen that was confirmed by in vitro transcription-translation technique combined with immunoblotting against rabbit anti-*M. paratuberculosis* hyperimmune serum and the nucleotide sequence of the 1402 bp that contains the p36K-encoding gene. Analyzing the recombinant clone pMptb #48 by SDS-immunoblotting technique with sera obtained from patients with mycobacterial and other diseases as well as controls, we were able serologically to group Crohn's disease (which has been linked with *M. paratuberculosis*) and sarcoidosis (a chronic granulomatous disease that has also been linked with mycobacterial infection) with other mycobacterial diseases. The results were: (Positive/total tested): 22/27 Crohn's disease (18.5%, 95% C.I.=62% to 94%), 4/6 tuberculosis (67%, 95% C.I.=22% to 96%), 6/6 leprosy, 5/5 sarcoidosis compared to 9/17 ulcerative colitis and 4/15 non-inflammatory bowel disease (non-IBD).

Rabbit hyperimmune anti-*M. paratuberculosis* serum was produced and adsorbed according to known methods (2,3). Rabbit hyperimmune anti-*M. avium* serum and serum from clinical cows with Johne's disease were obtained from Dr. M. Collins, University of Wisconsin, School of Veterinary Medicine, Madison, Wis. Serum from clinical sheep and goat with paratuberculosis were obtained from Allied Monitor, Inc., Fayette, Mo.. The efficiency of adsorption of each serum was evaluated by immunoblotting against *M. paratuberculosis* sonicate and non-recombinant *E. coli* lysate proteins fractionated on 12% SDS-PAGE (2). As a result of antibody screening, of our *M. paratuberculosis* (strain Linda) expression library, a total of 24 recombinant clones that reacted with the hyperimmune rabbit-antiserum were purified and analyzed by SDS-PAGE immunoblotting technique as described previously (3). Filter strips were incubated with adsorbed serum (diluted 1:500 for rabbit antiserum, 1:30 for animal sera and 1:50 for patient sera). The color detection was visualized with appropriate Anti-IgG peroxidase conjugates and 4-chloro-1-naphthol substrate.

To investigate whether the humoral immune response of CD patients would recognize any of the recombinant clones that were picked up and purified with rabbit anti-*M. paratuberculosis*, copies of SDS-immunoblot strips representing all 24 individually purified recombinants were tested. Seven of these clones reacted with the pooled CD patient sera; three were known to express the 65K heat shock protein (3). From the remaining four recombinants, one expressed 36K protein (P-36K) that reacted to the CD patient sera individually.

As discussed above, to compare the humoral reactivity of CD patients and patients with other mycobacterial diseases and controls with the clone expressing the P-36K, immunoblot strips containing this recombinant protein were tested with each individual adsorbed patient's serum. The results are shown in FIG. 2. Over 75% of tuberculosis and leprosy patients, and all BCG immunized individuals gave positive reactions with the P-36K protein. When the results of CD, sarcoidosis, ulcerative colitis, non-inflammatory bowel disease controls, and BCG negative individuals were compared, CD and sarcoidosis grouped with other mycobacterial diseases in regard to reactivity to P-36K. These results mimic the results with IS900-specific PCR-assays used to detect *M. paratuberculosis* in resected tissues of CD patients (1,4). In addition, all sera tested from patients with sarcoidosis were also positive with P-36K.

To determine if serum from animals with Johne's disease would recognize this P-36K recombinant clone, pooled serum from 3 cows, 2 sheep, and 2 goats, all with clinical symptoms, were tested separately. Only the goat serum reacted with P-36K protein. This indicates that the humoral immune response of different species respond differently to this antigen.

The foregoing results demonstrate that the mycobacterial recombinant protein from clone pMptb #48 and antigenic fragments thereof can be used in mycobacterial serological tests and for vaccine development.

In hybridization studies, the mycobacterial 1.4 kb BamH1-DNA insert from clone pMptb #48 hybridized to all mycobacterial species and none of the 20 related and unrelated organisms tested (FIG. 3). The nucleotide sequence for the 1.4 kb insert is shown in FIG. 4. These results demonstrate that this DNA fragment and sub-fragments thereof can be used as a genus-specific probe as well as to develop genus specific polymerase chain reaction (PCR) assay for the identification of mycobacteria. The sequence of this mycobacterial DNA fragment can be used as genus-specific probe and for the development of a mycobacteria-genus specific PCR assay.

REFERENCES

4. Dell'Isola, B., C. Poyart, O. Goulet, J. Mougenot, E. Sadoun-Journo, N. Brousse, J. Schmitz, C. Ricour, P. Berche. 1994. Detection of *Mycobacterium paratuberculosis* by polymerase chain reaction in children with Crohn's disease. J. Infect. Dis. 169:449–451.

6. El-Zaatari, F. A. KL, L. Engstrand, D. C. Markesich, and D. Y. Graham. 1992. Screening of a *Mycobacterium paratuberculosis* expression library with polyclonal antiserum and amplified DNA probes to identify species-specific immunodominant antigens. In R. J. Chiodini, Kreeger J. M. (eds): Proceedings of the Third International Colloquium on Paratuberculosis. Providence, R.I., USA: International Association for Paratuberculosis Inc, pp254–268.

7. El-Zaatari, F. A. K., S. Naser, L. Engstrand, C. Y. Hachem, and D. Y. Graham. 1994. Identification and characterization of *Mycobacterium paratuberculosis* recombinant clones expressed in *E. coli*. Current Microbiology 29: (in press).

16. Sanderson, J. D., M. T. Moss, M. L. Tizard, and J. Hermon-Taylor. 1992. *Mycobacterium paratuberculosis* DNA in Crohn's disease tissue. Gut 33:890–896.

I claim:

1. Recombinant clone pMptb #48.

2. An isolated nucleic acid comprising nucleotides in a sequence selected from the group consisting of the sequence of nucleotides 1–1402 of SEQ ID NO. 1 and the sequences of fragments thereof at least 15 nucleotides in length.

3. The isolated nucleic acid of claim 2, wherein said nucleotides are in a sequence selected from the group consisting of the sequence of nucleotides 372–1328 of SEQ ID NO. 1 and the sequences of fragments thereof at least 15 nucleotides in length.

4. A method for assessing the presence in a sample of nucleotide sequences which bind with a mycobacterial genus-specific nucleic acid probe comprising:

contacting a nucleic acid extract from said sample with a nucleic acid probe comprising nucleotides in a sequence selected from the group consisting of the sequence of nucleotides 1–1402 of SEQ ID NO. 1 and the sequences of fragments thereof at least 15 nucleotides in length;

allowing sufficient time for hybridization to occur between said nucleic acid probe and any complementary sequences in said sample of nucleotide sequences; and detecting the presence of any hybridization between said nucleic acid probe and complementary sequences in said sample of nucleotide sequences.

5. A method for amplifying DNA which codes for the protein coded by nucleotides 372–1328 of SEQ ID NO. 1, comprising:

selecting oligonucleotide primers designed on the basis of the sequence of nucleotides 1–1402 of SEQ ID NO. 1 or fragments thereof; and using polymerase chain reaction with said oligonucleotide primers to amplify said DNA which codes for the protein coded by nucleotides 372–1328 of SEQ ID NO. 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1402 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

GATCCCGACA CCACGTGGCC GTCCGCGGAG GTCACCCGGT AGTTGGCCGT GTAGGTCCCG 60

GCCGGCCCCA GCGGGCGCAC CGCCACGCTG ACCACCGCGT CCTGCACGGT GGGCTCTCCG 120

GTGGACCACA CGTTGCCGTC CGGCCCGACC ACCGTAATCG CGGCGAAGGT GGTTTGCAGC 180

-continued

| | | | | | |
|---|---|---|---|---|---|
| TGTTCGTTGA | AGGTCGCGCT | GACCCGGTGC | GGCCCGGTCG | TNAGCGCCGC | TTCGGCGGCG | 240 |
| GTNTCGGTCG | CCACCCGGNC | GGCGTGCGCC | CACGACGCGG | GCGCGGTCAG | CCCGGCGATC | 300 |
| AGGACCAGGG | CGCCGACGCA | CGCGCCAACC | GCCCAGCGCC | TCATGCCCGC | CGGCGGACCA | 360 |
| GGGCGATCGC | GATGCCCAGC | GCGGCCAGCA | CCAGCGCGGC | GCCGCCCAGC | CACCGCGCGG | 420 |
| CGTTGTCGGC | CGCGGCGGGT | CCGCCGGGGT | GCTGGTGGCC | GGCCGCCGGC | CGGCGGCAGG | 480 |
| GCGAGCGTCG | GGGCCGGGTG | CTCGGGCTCG | CCGCCGTCGG | GCAGCGGTGG | CTGATCCCAC | 540 |
| TTGACCACGG | TGCCGTCGGC | GTAGGTCTGG | NTGGCCGGAA | AGCTGACGGT | GTCGGCGTCG | 600 |
| GGCAGCTTCA | CCGACAGCCG | GAACAGGGCG | AACTGGTCGG | GCCCGATGCC | GCCGCCCGCG | 660 |
| GGGGTTCCCA | GGTGACCGAG | CGGACGGTGC | CGGATGCCGC | GTCCCGGTCC | AGCCGGGCCG | 720 |
| TCCAGCCCGG | CATGGTCTCG | GTGTGCGCCG | CGGCCACGTT | GGGCAGCGCG | ACGGTCAGCG | 780 |
| CGGTGGTGGC | GGCCCCGGTG | TTCGATTCGT | TGGGCACCTG | GAAGGTGACG | ACGGCCATGG | 840 |
| CGCCGCGCAC | CGGGTTGTCG | CTGCCGGCGT | GCACGTGCGC | CGACGCCATC | GGGGACCAGG | 900 |
| CCACCGATCC | CAGGCACAGG | GCGGCGACGG | CGACCAGCAG | GCGCGGGGCC | CGGCGCTTGC | 960 |
| GCGGCGGCAT | GCGGGTAGCT | CAACCCGAGG | CGGGCCATCA | GGTCCGCCTC | GATGCCGTCG | 1020 |
| AGCTGCGAGG | AGATGGCGGC | GTGTCCCGCC | CGGCGCCGGG | CGGCGGGCAT | GTTCTCCGCG | 1080 |
| GCGGTCACCG | CGGCCGCCAG | GTCGGTGAGC | CGCTCGGAGA | TGGCGGCGAC | GAACTGCTTG | 1140 |
| GTCTCGCCGT | CCTTGGTTTG | CGTTCCTGCA | CCAGCCGCAA | CGACTTCTCC | GCCCCGGCGA | 1200 |
| TGCGGGCCGA | CAGCTGGGCG | CCGTGGCCGG | AGAACTGGCC | GATCTGGGCC | AACGGGACGC | 1260 |
| CCAGCCGATC | GGCGCGGCGC | TGGTCGATCA | GCGCGCGCGC | CGAGACGGGG | CGCGGTAGAC | 1320 |
| GAACGGGGTG | AGGATCGGGG | CGAACAGCCG | GACAACGTGA | GGTCCGAGCT | CGGTACAAGT | 1380 |
| TGGATGATAG | TTGATTTCTT | TG | | | | 1402 |

( 2 ) INFORMATION FOR SEQ ID NO:2:

( i ) SEQUENCE CHARACTERISTICS:
        ( A ) LENGTH: 465 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:2:

```
Ser Arg His His Val Ala Val Arg Gly Gly His Pro Val Val Gly Arg
  1               5                  10                  15

Val Gly Pro Gly Arg Pro Gln Arg Ala His Arg His Ala Asp His Arg
             20                  25                  30

Val Leu His Gly Gly Leu Ser Gly Gly Pro His Val Ala Val Arg Pro
         35                  40                  45

Asp His Arg Asn Arg Gly Glu Gly Gly Leu Gln Leu Phe Val Glu Gly
     50                  55                  60

Arg Ala Asp Pro Val Arg Pro Gly Arg Xaa Arg Arg Phe Gly Gly Gly
 65                  70                  75                  80

Xaa Gly Arg His Pro Xaa Gly Val Arg Pro Arg Arg Gly Arg Gly Gln
                 85                  90                  95

Pro Gly Asp Gln Asp Gln Gly Ala Asp Ala Arg Ala Asn Arg Pro Ala
            100                 105                 110

Pro His Ala Arg Arg Arg Thr Arg Ala Ile Ala Met Pro Ser Ala Ala
        115                 120                 125
```

-continued

| | | | | | | | | | | | | | | | |
|---|---|---|---|---|---|---|---|---|---|---|---|---|---|---|---|
| Ser | Thr | Ser | Ala | Ala | Pro | Pro | Ser | His | Arg | Ala | Ala | Leu | Ser | Ala | Ala |
| | 130 | | | | | 135 | | | | | 140 | | | | |
| Ala | Gly | Pro | Pro | Gly | Cys | Trp | Trp | Pro | Ala | Ala | Gly | Arg | Arg | Gln | Gly |
| 145 | | | | | 150 | | | | | 155 | | | | | 160 |
| Glu | Arg | Arg | Gly | Arg | Val | Leu | Gly | Leu | Ala | Ala | Val | Gly | Gln | Arg | Trp |
| | | | | 165 | | | | | 170 | | | | | 175 | |
| Leu | Ile | Pro | Leu | Asp | His | Gly | Ala | Val | Gly | Val | Gly | Leu | Xaa | Gly | Arg |
| | | | 180 | | | | | 185 | | | | | 190 | | |
| Lys | Ala | Asp | Gly | Val | Gly | Val | Gly | Gln | Leu | His | Arg | Gln | Pro | Glu | Gln |
| | | 195 | | | | | 200 | | | | | 205 | | | |
| Gly | Glu | Leu | Val | Gly | Pro | Asp | Ala | Ala | Ala | Arg | Gly | Gly | Ser | Gln | Val |
| | 210 | | | | | 215 | | | | | 220 | | | | |
| Thr | Glu | Arg | Thr | Val | Pro | Asp | Ala | Ala | Ser | Arg | Ser | Ser | Arg | Ala | Val |
| 225 | | | | | 230 | | | | | 235 | | | | | 240 |
| Gln | Pro | Gly | Met | Val | Ser | Val | Cys | Ala | Ala | Ala | Thr | Leu | Gly | Ser | Ala |
| | | | | 245 | | | | | 250 | | | | | 255 | |
| Thr | Val | Ser | Ala | Val | Ala | Ala | Pro | Val | Phe | Asp | Ser | Leu | Gly | Thr | Trp |
| | | | 260 | | | | | 265 | | | | | 270 | | |
| Lys | Val | Thr | Thr | Ala | Met | Ala | Pro | Arg | Thr | Gly | Leu | Ser | Leu | Pro | Ala |
| | | 275 | | | | | 280 | | | | | 285 | | | |
| Cys | Thr | Cys | Ala | Asp | Ala | Ile | Gly | Asp | Gln | Ala | Thr | Asp | Pro | Arg | His |
| | 290 | | | | | 295 | | | | | 300 | | | | |
| Arg | Ala | Ala | Thr | Ala | Thr | Ser | Arg | Arg | Gly | Ala | Arg | Arg | Leu | Arg | Gly |
| 305 | | | | | 310 | | | | | 315 | | | | | 320 |
| Gly | Met | Arg | Val | Ala | Gln | Pro | Glu | Ala | Gly | His | Gln | Val | Arg | Leu | Asp |
| | | | | 325 | | | | | 330 | | | | | 335 | |
| Ala | Val | Glu | Leu | Arg | Gly | Asp | Gly | Gly | Val | Ser | Arg | Pro | Ala | Pro | Gly |
| | | | 340 | | | | | 345 | | | | | 350 | | |
| Gly | Gly | His | Val | Leu | Arg | Gly | Gly | His | Arg | Gly | Arg | Gln | Val | Gly | Glu |
| | | 355 | | | | | 360 | | | | | 365 | | | |
| Pro | Leu | Gly | Asp | Gly | Gly | Asp | Glu | Leu | Leu | Gly | Leu | Ala | Val | Leu | Gly |
| | 370 | | | | | 375 | | | | | 380 | | | | |
| Leu | Arg | Ser | Cys | Thr | Ser | Arg | Asn | Asp | Phe | Ser | Ala | Pro | Ala | Met | Arg |
| 385 | | | | | 390 | | | | | 395 | | | | | 400 |
| Ala | Asp | Ser | Trp | Ala | Pro | Trp | Pro | Glu | Asn | Trp | Pro | Ile | Trp | Ala | Asn |
| | | | | 405 | | | | | 410 | | | | | 415 | |
| Gly | Thr | Pro | Ser | Arg | Ser | Ala | Arg | Arg | Trp | Ser | Ile | Ser | Ala | Arg | Ala |
| | | | 420 | | | | | 425 | | | | | 430 | | |
| Glu | Thr | Gly | Arg | Gly | Arg | Arg | Thr | Gly | Xaa | Gly | Ser | Gly | Arg | Thr | Ala |
| | | 435 | | | | | 440 | | | | | 445 | | | |
| Gly | Gln | Arg | Glu | Val | Arg | Ala | Arg | Tyr | Lys | Leu | Asp | Asp | Ser | Xaa | Phe |
| | 450 | | | | | 455 | | | | | 460 | | | | |
| Leu | | | | | | | | | | | | | | | |
| 465 | | | | | | | | | | | | | | | |